United States Patent [19]

Aho et al.

[11] Patent Number: 5,001,152

[45] Date of Patent: Mar. 19, 1991

[54] USE OF CATECHOL-O-METHYL TRANSFERASE (COMT) INHIBITORS AND THEIR PHYSIOLOGICALLY ACCEPTABLE SALTS FOR ULCER TREATMENT

[75] Inventors: Päivi A. Aho; Pentti Pohto; Inge-Britt Y. Lindén; Reijo J. Bäckström, all of Helsinki; Erkki J. Honkanen, Vantaa; Erkki A. O. Nissenen, Espoo, all of Finland

[73] Assignee: Orion Corporation Ltd., Espoo, Finland

[21] Appl. No.: 288,979

[22] Filed: Dec. 23, 1988

[30] Foreign Application Priority Data

Dec. 24, 1987 [GB] United Kingdom ............ 8730190
Sep. 1, 1988 [GB] United Kingdom ............ 8820729

[51] Int. Cl.$^5$ ............ A61K 31/235; A61K 31/275; C07C 255/00; C07C 69/00
[52] U.S. Cl. ............ 514/519; 514/520; 514/557; 514/731; 514/737; 514/925; 514/926; 514/927; 558/412; 560/130
[58] Field of Search ............ 514/520, 925, 926, 927, 514/731, 737, 557

[56] References Cited

U.S. PATENT DOCUMENTS

| | | | |
|---|---|---|---|
| 4,436,752 | 3/1984 | Christidis et al. | 424/317 |
| 4,760,089 | 7/1988 | Chambers et al. | 514/523 |

FOREIGN PATENT DOCUMENTS

| | | | |
|---|---|---|---|
| 0081321 | 6/1983 | European Pat. Off. | |
| 0125919 | 11/1984 | European Pat. Off. | |
| 237929 | 3/1987 | European Pat. Off. | 514/520 |
| 0149407 | 4/1987 | European Pat. Off. | |
| 0149952 | 7/1987 | European Pat. Off. | |
| 0282898 | 3/1988 | European Pat. Off. | |
| 864875 | of 0000 | Finland . | |
| 871564 | 3/1987 | South Africa . | |
| 902586 | 8/1962 | United Kingdom . | |
| 1188364 | 4/1970 | United Kingdom . | |
| 1276966 | 6/1972 | United Kingdom . | |
| 2008103A | 5/1979 | United Kingdom . | |

OTHER PUBLICATIONS

Chemical Abstracts, vol. 102, No. 9, Mar. 4, 1985, Abstract 72397g, Barnaulov O.D.
Backstrom et al. "Synthesis . . . ", CA 110:172835g (1989).
Backstrom et al, "Preparation . . . "; CA 109:128570x (1988).
Iida et al, Chemical Abstracts vol. 79:105449n, p. 447 (1973).
Castello et al, Chemical Abstracts, vol. 104:109112e, p. 676 (1986).
Vellaccio et al, Chemical Abstracts, vol. 95:42542v, p. 710 (1981).
Umemura et al, Chemical Abstracts, vol. 92:146461x, p. 560 (1980).
Firnau et al, Chemical Abstracts, vol. 79:27554b, p. 65 (1973).
Windholz et al, The Merck Index, p. 1022 (1976), Items 7678 and 7679.

Primary Examiner—Mukund J. Shah
Assistant Examiner—Celia Chang
Attorney, Agent, or Firm—Burns, Doane, Swecker & Mathis

[57] ABSTRACT

The invention is concerned with the new use of known catechol derivatives of the formula

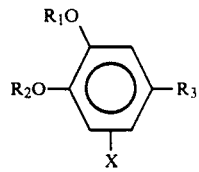

wherein $R_1$ and $R_2$ are each hydrogen, alkyl having 1 to 4 carbon atoms or alkanoyl having 2 to 5 carbon atoms; X is nitro, halogen or cyano and $R_3$ is chlorine, nitro, cyano or a radical of the formula

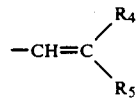

wherein $R_4$ is hydrogen, cyano, alkyl having 1 to 4 carbon atoms or alkanoyl having 2 to 5 carbon atoms and $R_5$ is cyano, alkanoyl having 2 to 5 carbon atoms, hydroxyalkyl having 1 to 4 carbon atoms, carboxyl or phenylcarbonyl unsubstituted or substituted with one to three methoxy groups or pharmaceutically acceptable salt thereof. The new use is the treatment and prophylaxis of ulcers and lesions in the gastrointestinal tract.

22 Claims, No Drawings

USE OF CATECHOL-O-METHYL TRANSFERASE (COMT) INHIBITORS AND THEIR PHYSIOLOGICALLY ACCEPTABLE SALTS FOR ULCER TREATMENT

The present invention relates to use of catechol-O-methyl transferase (COMT) inhibitors.

Such compounds are known and have been described e.g. in Finnish patent application 864875 and in European patent application 237929 as COMT inhibitors and they have been shown to be effective medicaments for treating for instance, Parkinsonism.

It has now unexpectedly been found that COMT-inhibitors may be used for the treatment and prophylaxis of ulcers and lesions and similar conditions in the gastrointestinal tract.

The above compounds may be shown by following general formula I

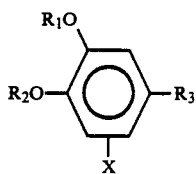

wherein $R_1$ and $R_2$ independently comprise hydrogen, alkyl, optionally substituted acyl or optionally substituted aroyl, lower alkylsulfonyl or alkylcarbamoyl or taken together form a lower alkylidene or cycloalkylidene group, X comprises electronegative substituent such as halogen, nitro, cyano, lower alkylsulfonyl, sulfonamido, trifluoromethyl, aldehyde or carboxyl and $R_3$ comprises hydrogen, halogen, substituted alkyl, hydroxyalkyl, nitro, cyano, optionally substituted amino, trifluoromethyl, lower alkylsulfonyl, sulfonamido, aldehyde, alkylcarbonyl, aralkylidenecarbonyl or carboxyl group or a group selected from

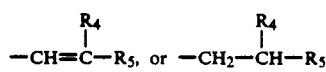

wherein $R_4$ comprises hydrogen, alkyl, amino, cyano, carboxyl or acyl and $R_5$ comprises hydrogen, amino, cyano, carboxyl, alkoxycarbonyl, carboxyalkenyl, nitro, acyl, hydroxyalkyl, carboxyalkyl, COZ, wherein Z is an optionally substituted heterocyclic ring or one of following optionally substituted groups; carboxamido, carbamoyl, aroyl or heteroaryl or $R_4$ and $R_5$ together form a five to seven membered substituted cycloalkanone ring;

wherein n is 0-1, m is 0-7 and R comprises alkyl, hydroxy, carboxyalkyl, optionally substituted alkene, optionally substituted heterocyclic ring, alkoxy or substituted amino;

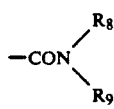

wherein $R_8$ and $R_9$ independently comprise hydrogen or one of the following optionally substituted groups; alkyl, alkenyl, alkynyl, cycloalkyl, aralkyl or taken together form an optionally substituted piperidyl group;

wherein $R_{10}$ comprises a substituted alkyl group;

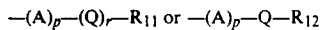

wherein p is 0 or 1, r is 0 or 1, A comprises a vinylene group, optionally substituted with lower alkyl, $R_{11}$ comprises —$COR_{13}$, carbocyclic, aromatic group or aromatic or partially unsaturated heterocyclic group bound through a carbon atom, $R_{12}$ comprises hydrogen or an optionally substituted saturated or partially unsaturated lower hydrocarbon group, $R_{13}$ comprises hydroxy, amino, optionally substituted saturated or or partially unsaturated lower hydrocarbon group being bound by the aid of an oxygen atom or an imino or lower alkyl-imino group or a saturated nitrogen containing heterocyclic group bound through the nitrogen atom in the ring, Q comprises —CO— or >C=N—(B-)$_s$—$R_{14}$, wherein B comprises an oxygen atom or an imino group, s is 0 or 1 and $R_{14}$ comprises hydrogen, an optionally substituted saturated or partially unsaturated lower hydrocarbon group optionally bound through a carbonyl group.

In the above patent applications it has been described several methods for the preparation of the compounds according to formula I. The methods for the preparation of esters which, when given to a patient, mostly hydrolyze readily to the active compound have been described in these publications too.

Salts of these compounds, when applicable, may be prepared by known methods. All physiologically acceptable salts are useful as active medicaments, however, preferred are the salts with hydrochloric, hydrobromic, phosphoric and sulfuric acids and with the organic acids like oxalic, fumaric, tartaric, malonic, acetic and citric acids etc.

Peptic ulcer is a pluricausal disease, the pathogenesis and cause of which are not yet fully understood. Duodenal ulcer is the most prevalent form of peptic ulcers. Thus cysteamine-induced duodenal ulcer in rats, an animal model which morphologically and functionally resembles human duodenal ulcer (Szabo, S. Lab. Invest. 51:121-147, 1984), has offered a useful possibility to test the antiulcer drugs and study the pathophysiology of ulceration. Besides the known antiulcer drugs, also dopamine and dopamine agonists are found to be protective in this animal model, whereas dopamine antagonists aggravate the ulcers (Horner, H.C., Szabo, S., Life Sci. 29:2437-2443, 1981). Decreased dopamine levels after cysteamine are detected in gastric and duodenal mucosa (Szabo, S. et al. J.Pharmacol. Exp. Ther. 240:871-878, 1987). Dopamine is also known to influence the gastric secretion, gastroduodenal motility and intestinal blood flow, which are all involved in the pathogenesis of ulceration.

The present compounds are effective in treating various conditions in which lesions are located in the esophagus, stomach, small intestine, colon or rectum or for prophylaxis of the lesions in the gastrointestinal tract. Illnesses which at least can be treated with the compounds are for instance ulcers in the esophagus, duodenal or ventricular ulcers, gastritis, ulcerative colitis or ulcers in the rectum or minor lesions in the gastrointestinal tract.

In the preferred compounds X is nitro or cyano especially in the 5-position. In these compounds $R_3$ is especially nitro, cyano, halogen or a group which has a conjugated double bond system with the double bonds of the aromatic ring whereto $R_3$ is attached. Thus preferred compounds are for instance those having $R_3$ which begins with a single bond (the attaching bond) and continues with a double bond in the main chain or in the side chain. The double bonds are in many cases located between two carbon atoms or between a carbon atom and oxygen atom. Because the conjugated system may be quite long, there may be also present both types of double bonds and also rings having double bonds may be involved in the conjugated system.

The effective dose varies considerably depending of whether the compounds are given for prophylaxis or for treatment of peptic ulcers. The daily dose and the number of doses are dependent of the severity on the illness to be treated. As far as it is possible now to predict the effective dose for human beings, it may be said that the effective dose is from about 1 to 100 mg per day once a day or divided into several doses. The preferred dose may be from about 10 to 60 mg per day.

The compounds according to this invention are formulated into dosage forms using the principles which are known to the man having average skills in the art. The compounds according to this invention are given to a patient as such or in combination with suitable pharmaceutical material in the form of tablets, dragees, capsules, suppositories, emulsions, suspensions or solutions whereby the contents of the active compound is in the formulation from 1 to 100 weight-%.

Choosing the auxiliary ingredients for the formulation is a task of the experienced staff in the art. It is evident that suitable solvents, gel forming ingredients, dispersion forming ingredients, antioxidants, colors etc are used in a normal way.

The compositions are given enterally or parenterally, the oral way being the easiest and preferred way.

The compositions are formulated for the purpose of the medicine, normal uncoated tablets being quite satisfactory when lesions located in the stomach area are treated. When the lesions are located in the small intestine or in the colon it is advisable to use coated tablets, so called enterotablets to secure that the medicine reaches the desired part of the gastrointestinal tract. When the lesion of rectum are treated, suppositories are the normal way to give the medicine. Suppositories are also given when the desired systemic effect is desired with patients having nausea and the like symptoms.

EXAMPLE 1

Cysteamine-Induced Duodenal Ulcer in Rats

Cysteamine-induced duodenal ulcer in rats resembles morphologically and functionally human duodenal ulcer. All known antiulcer drugs are found to be effective in this model.

Test compounds were administered orally half an hour before s.c. cysteamine 425 mg/kg. The rats were sacrificed 24 hours after cysteamine and the ulcer index for the duodenum was calculated. The ulcer index is the sum of (1) percent incidence (divided by 10) of animals with ulcers, (2) average severity of ulcers per rat for each group, (3) average number of duodenal ulcers per rat for each group. The severity of ulcers was evaluated on a scale of 0 to 3, where 0=normal duodenum, 1=erosion (lesion limited to mucosa), 2=deep ulcer involving the muscularis propria, 3=penetrated or perforated ulcer.

The results are summarized in TABLE 1.

TABLE 1

The preventing effect of the catechol derivatives on cysteamine-induced duodenal ulcer after a single dose.

| dose mg/kg p.o. | Control | OR-462 10 | OR-462 30 | OR-486 10 | OR-486 30 |
|---|---|---|---|---|---|
| n | 11 | 8 | 8 | 8 | 7 |
| Incidence of ulcers (%) | 91 | 75 | 25 | 63 | 43 |
| Severity of ulcers (0-3) | 1.8 | 1.3 | 0.4 | 0.7 | 0.4 |
| Number of ulcers in duodenum | 1.9 | 0.9 | 0.4 | 1.0 | 0.6 |
| Ulcer index | 12.8 | 9.7 | 3.3 | 8.0 | 5.3 |
| Reduction (%) | | 24 | 74 | 38 | 59 |

OR-462 = 3-(3,4-dihydroxy-5-nitrobenzylidene)-2,4-pentanedione
OR-486 = 3,5-dinitrocatechol

EXAMPLE 2

In this example the compounds were dosed twice, the first dose was administered as in Example 1 and the other dose was given again 5 hours after cysteamine. The rats were sacrificed 24 hours after cysteamine and the ulcer index for the duodenum was calculated as in Example 1. The results are given in TABLE 2.

TABLE 2

The preventing effect of OR-462 b.i.d. on cysteamine-induced duodenal ulcer.

| dose mg/kg p.o. | Control | OR-462 2 × 5 | OR-462 2 × 10 |
|---|---|---|---|
| n | 8 | 8 | 8 |
| Incidence of ulcers (%) | 100 | 50 | 38 |
| Severity of ulcers (0-3) | 1.8 | 0.8 | 0.9 |
| Number of ulcers in duodenum | 1.9 | 0.5 | 0.6 |
| Ulcer index | 13.7 | 6.3 | 5.3 |
| Reduction (%) | | 54 | 61 |

The compounds OR-462 and OR-486 significantly reduced both incidence and severity of cysteamine-induced duodenal ulcers. When administered twice a day the potency of PR-462 was even more pronounced. The results indicate a possible effect of these compounds also in human duodenal ulcer.

EXAMPLE 3

Ethanol-Induced Gastric Lesions in Rats

Oral administration of absolute ethanol to rats results in severe gastric damage consisting of grossly hemorrhagic and necrotic lesions.

Rats were orally dosed with test compounds. Half an hour later the rats were orally administered with 1 ml of absolute ethanol. The animals were sacrificed one hour after ethanol and the total area of lesions in each stomach was examined.

The results are given in TABLE 3

TABLE 3

The effect of the catechol derivatives on the area of ethanol-induced gastric damage in rats.

| dose mg/kg p.o. | Control | OR-462 10 | OR-462 30 | OR-486 10 | OR-486 30 |
|---|---|---|---|---|---|
| n | 20 | 8 | 7 | 8 | 8 |

TABLE 3-continued

The effect of the catechol derivatives on the area of ethanol-induced gastric damage in rats.

| dose mg/kg p.o. | Control | OR-462 10 | OR-462 30 | OR-486 10 | OR-486 30 |
|---|---|---|---|---|---|
| Area of lesions | 92.4 | 58.1* | 35.3** | 55.1* | 15.3** |
| SE | ±9.5 | ±18.5 | ±8.9 | ±5.4 | ±7.7 |
| Inhibition % |  | 37 | 62 | 40 | 83 |

*$p \leq 0.05$
**$p \leq 0.01$ vs. control

Both compounds, OR-462 and OR-486 reduced significantly the area involved in ethanol-induced gastric lesions. This finding implies a cytoprotective effect of these compounds.

TABLE 4

The effect of some test compounds on the area of ethanol-induced gastric damage in rats. The mean area of lesions of control rats was $79.8 \pm 8$ mm$^2$ and the extent of damage in duodenum $4 \pm 1$ cm (n = 39).

| Compound No | Dose mg/kg p.o. | Reduction in lesion area % (ventricle) | Reduction in lesion length % (duodenum) |
|---|---|---|---|
| A | 100 | 93 | 90 |
| B | 100 | 88 | 73 |
| C | 100 | 58 | 70 |
| D | 100 | 83 | 86 |

The compounds were:

(A) 3-(3-hydroxy-4-methoxy-5-nitrobenzylidene)-2,4-pentanedione (B) 3-(4-hydroxy-3-methoxy-5-nitrobenzylidene)-2,4-pentanedione (C) 3-(3-chloro-5-ethoxy-4-hydroxybenzylidene)-2,4-pentanedione (D) 3-(3-chloro-4,5-dihydroxybenzylidene)-2,4-pentanedione

EXAMPLE 4

An oral composition in the form of a tablet was made in accordance with the following formulation.

| The effective compound (e.g. OR-462) | 30.0 mg |
|---|---|
| Lactos. | 120.0 mg |
| Mayd.amyl. | 65.0 mg |
| Gelatin | 4.5 mg |
| Aq.purif. | about 44.0 mg* |
| Mayd.amyl. | 10.0 mg |
| Talc. | 9.0 mg |
| Magn. stear. | 1.8 mg |

*evaporates during processing

The procedure was so called Glatt-process in which the active ingredient is first granulated with the auxiliary ingredients and the granules are then pressed into tablets.

We claim:

1. A method for the prevention or treatment of ulcers or lesions in the gastrointestinal tract, said method comprising administering a therapeutically effective amount to prevent or treat ulcers or lesions in the gastrointestinal tract of a compound of formula I

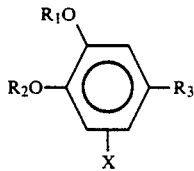

wherein $R_1$ and $R_2$ are each hydrogen, alkyl having 1 to 4 carbon atoms or alkanoyl having 2 to 5 carbon atoms; X is nitro, halogen or cyano and $R_3$ is chlorine, nitro, cyano or a radical of the formula

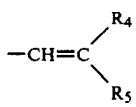

wherein $R_4$ is hydrogen, cyano, alkyl having 1 to 4 carbon atoms or alkanoyl having 2 to 5 carbon atoms and $R_5$ is cyano, alkanoyl having 2 to 5 carbon atoms, hydroxyalkyl having 1 to 4 carbon atoms, carboxyl or phenylcarbonyl unsubstituted or substituted with one to three methoxy groups or pharmaceutically acceptable salt thereof to a patient in need of such treatment.

2. The method as claimed in claim 1, wherein $R_1$ and $R_2$ are independently selected from hydrogen and alkanoyl having 2 to 5 carbon atoms.

3. The method as claimed in claim 1, wherein X is cyano or nitro.

4. The method as claimed in claim 1, wherein $R_3$ is chlorine, nitro, cyano or a radical of the formula

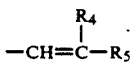

wherein $R_4$ is cyano or alkanoyl having 2 to 5 carbon atoms and $R_5$ is cyano or alkanoyl having 2 to 5 carbon atoms.

5. The method as claimed in claim 4, wherein both $R_4$ and $R_5$ are alkanoyl having 2 to 5 carbon atoms.

6. The method as claimed in claim 1, wherein the compound is 3,5-dinitrocatechol.

7. The method as claimed in claim 1, wherein the compound is 3,4-dihydroxy-5-nitro-ω,ω-dicyanostyrene.

8. The method as claimed in claim 1, wherein the compound is 4-(3,4-dihydroxy-5-nitrophenyl)-3-methyl-but-3-en-2-one.

9. The method as claimed in claim 1, wherein the compound is 3-(3,4-dihydroxy-5-nitrophenyl)-1-(3,4,5-trimethoxyphenyl)-prop-2-en-1-one.

10. The method as claimed in claim 1, wherein the compound is 3-(3,4-dihydroxy-5-nitrophenyl)-1-phenyl-prop-2-en-1-one.

11. The method as claimed in claim 1, wherein the compound is 4-(3,4-dihydroxy-5-nitrophenyl)-3-methyl-but-3-en-2-ol.

12. The method as claimed in claim 1, wherein the compound is 4-hydroxy-3-methoxy-5-nitrocinnamic acid.

13. The method as claimed in claim 1, wherein the compound is 1,2-diacetoxy-3,5-dinitrobenzene.

14. The method as claimed in claim 1, wherein the compound is 3,4-dihydroxy-5-nitrobenzonitrile.

15. The method as claimed in claim 1, wherein the compound is 4-chloro-6-nitrocatechol.

16. The method as claimed in claim 1, wherein the compound is 1,2-dipropionyloxy-3,5-dinitrobenzene.

17. The method as claimed in claim 1, wherein the compound is 2-pivaloyloxy-4,6-dinitrophenol.

18. The method as claimed in claim 1, wherein the compound is 3-(3-hydroxy-4-methoxy-5-nitrobenzylidene)-2,4-pentanedione.

19. The method as claimed in claim 1, wherein the compound is 3-(4-hydroxy-3-methoxy-5-nitrobenzylidene)-2,4-pentanedione.

20. The method as claimed in claim 1, wherein the compound is 3-(3-chloro-5-ethoxy-4-hydroxybenzylidene)-2,4-pentanedione.

21. The method as claimed in claim 1, wherein the compound is 2-(3-chloro-4,5-dihydroxybenzylidene)-2,4-pentanedione.

22. A method for the prevention or treatment of ulcers or lesions in the gastrointestinal tract, said method comprising administering a therapeutically effective amount of 3-(3,4-dihydroxy-5-nitrobenzylidene)-2,4-pentanedione or pharmaceutically acceptable salt thereof to prevent or treat ulcers or lesions in the gastrointestinal tract to a patient in need of such prevention or treatment.

* * * * *